(12) United States Patent
Connelly et al.

(10) Patent No.: US 7,169,575 B2
(45) Date of Patent: Jan. 30, 2007

(54) HOMOCYSTEINE ASSAY (75) Inventors: Caroline Connelly, Dundee (GB); Jeff Brady, Dundee (GB)

(73) Assignee: Axis Shield plc, Dundee (GB)

(*) Notice: Subject to any disclaimer, the term of this patent is extended or adjusted under 35 U.S.C. 154(b) by 645 days.

(21) Appl. No.: 09/857,433

(22) PCT Filed: Apr. 10, 2001

(86) PCT No.: PCT/GB01/01615
§ 371 (c)(1),
(2), (4) Date: Mar. 5, 2002

(87) PCT Pub. No.: WO01/77670

PCT Pub. Date: Oct. 18, 2001

(65) Prior Publication Data
US 2003/0040030 A1  Feb. 27, 2003

(30) Foreign Application Priority Data
Oct. 4, 2000 (GB) .................. 0008784.1

(51) Int. Cl.
*C12Q 1/26* (2006.01)
(52) U.S. Cl. ........................................ 435/25
(58) Field of Classification Search .................. 435/25, 435/4, 15, 18, 26, 7.72; 436/825
See application file for complete search history.

(56) References Cited

U.S. PATENT DOCUMENTS

| | | | | |
|---|---|---|---|---|
| 5,885,767 A | * | 3/1999 | Rozzell, Jr. | 435/4 |
| 5,985,540 A | | 11/1999 | Tan et al. | |
| 5,998,191 A | * | 12/1999 | Tan et al. | 435/232 |
| 6,066,467 A | * | 5/2000 | Xu et al. | 435/23 |
| 6,306,618 B1 | * | 10/2001 | Coombs et al. | 435/18 |
| 6,635,438 B2 | * | 10/2003 | Kawasaki et al. | 435/25 |
| 6,686,172 B2 | * | 2/2004 | Matsuyama et al. | 435/18 |

FOREIGN PATENT DOCUMENTS

| | | |
|---|---|---|
| EP | 0 726 322 A1 | 8/1996 |
| WO | WO93/15220 A2 | 8/1993 |
| WO | WO98/07872 A2 | 2/1998 |
| WO | WO98/59242 A1 | 12/1998 |
| WO | WO00/00821 A1 | 1/2002 |

* cited by examiner

*Primary Examiner*—Ralph Gitomer
(74) *Attorney, Agent, or Firm*—Bacon & Thomas (57) ABSTRACT

The present invention provides an improved method of assessing/quantifying the amount of homocysteine in a body fluid sample via an enzymatic assay. The assay includes steps of reducing background signal by treatment with one of the following: a reducing agent, a pyruvate deactivating agent, heat treatment, or by lyophilising or immobilizing the homocysteine converting enzyme.

4 Claims, 4 Drawing Sheets

HOMOCYSTEINE ASSAY

This application is a 371 application of PCT/GB01/01615 filed Apr. 10, 2001 and which claims priority from United Kingdom patent application number GB 0008784.1, filed Oct. 4, 2000.

FIELD OF THE INVENTION

The present invention relates to improvements in and relating to enzymatic assays for homocysteine in biological fluid samples.

BACKGROUND OF THE INVENTION

Elevated blood plasma homocysteine levels can be correlated to risk of cardiovascular disease, e.g. coronary heart disease, coronary artery disease, cerebrovascular disease, and peripheral vascular disorders. Indeed elevated homocysteine levels are thought to be a better predictor of cardiovascular disease than elevated cholesterol levels. Generally plasma levels of 15 µM and below are considered healthy (see for example New England Journal of Medicine 1997, 337: 230).

Accordingly there is a need for reliable methods for determining homocysteine levels in patients.

Direct determination of homocysteine has thus far proved to be complicated, e.g. because it has not been found possible to raise an antibody against homocysteine (HCy) which is not cross-reactive with other substances present in biological samples.

However, in WO 93/15520 (Axis) and WO 98/07872 (Glasgow) for example, homocysteine assays are described which involve enzymatic conversion of homocysteine and determination of homocysteine levels by determination of a homocysteine conversion product produced by the enzyme-mediated conversion.

Such assays require the use of a reducing agent (e.g. dithiothreitol) to liberate covalently bound homocysteine and of a homocysteine converting enzyme and while they perform well there is room for improvement in terms of increasing signal to noise, e.g. by reducing background signal.

BRIEF SUMMARY OF THE INVENTION

We have now surprisingly found that the performance of such enzymatic HCy assays may be improved by a variety of relatively simple measures.

A first of such measures involves treatment of the biological fluid sample with a reducing agent for example a thiol (particularly a dithiol, such as dithiothreitol (DTT), dithioerythrol (DTE) or bis-(2-mercaptoethyl)sulphone), phosphine (e.g. triscarboxyethylphosphine (TCEP) or tri-n-butyl-phosphine), methyl iodide, thioredoxin, lipoic acid or a borohydride) to liberate covalently bound homocysteine, addition of a homocysteine converting enzyme and then treatment of the sample with an agent which neutralizes the reducing agent, e.g. one which binds to it, oxidizes it or otherwise depotentiates it, for example an organic disulphide compound or a dithiol (especially DTT or DTE) binding agent.

Viewed from one aspect therefore the invention provides an assay for homocysteine which comprises contacting a biological fluid sample with a reducing agent, especially DTT or DTE, and subsequently with homocysteine desulphurase, characterised in that said sample is contacted with an agent which binds, oxidizes or depotentiates said reducing agent, e.g. an organic disulphide or a dithiol (especially DTT or DTE) binding or depotentiating agent, for example cystamine or a maleimide, after being contacted with said homocysteine desulphurase.

Examples of suitable binding agents for thiol-based reducing agents such as DTT and DTE include maleimides, particular cyclic N-maleimides, i.e. optionally 3 and or 4-substituted, N-substituted 1-aza-2,5-dioxo-cyclopentenes, particularly compounds in which the N-substitution is to produce a bis maleimide and wherein the ring C and N substituents contain up to 25 carbons (e.g. comprising alkyl, aryl, aralkyl, aralkyl and maleimide groups). Examples of particular maleimides include N-methyl-maleimide, N-ethyl-maleimide, 1,1'-(3,3'-dimethyl-1,1'-biphenyl-4,4'-diyl)-bismaleimide, 1,1'-(methylene di-4,1-phenylene)bismaleimide, N-(1-phenylethyl)maleimide, 1-(2-methoxy-5-methyl phenyl) maleimide, and 2-methyl-N-phenyl-maleimide. Many of these compounds are available commercially, e.g. from Sigma Aldrich. Examples of other suitable dithiol depotentiating agents include cystamine and other compounds that reduce the reducing capacity of dithiols such as DTT, oxiranes, aziridines, aryl halides, mercurials (e.g. p-chloromercuribenzene sulphonic acid and hydroxymercuribenzoic acid), vinyl sulphones, haloacetyl compounds (e.g. iodoacetimide), 5,5-dithio-bis(2-nitro benzoic acid) (i.e. Ellman's Reagent) and disulphide exchange reagents such as pyridyl sulphides (e.g. 4,4-dipyridyl-disulphide).

The reducing agent (e.g. DTE, DTT or TCEP) is conveniently added to the biological fluid sample at a concentration of 0.5 to 5 mM, especially preferably about 1 mM. Where the reducing agent is not a dithiol, an organic disulphide rather than a dithiol binding or depotentiating agent will be used. The organic disulphide or dithiol binding or depotentiating agent is typically added to a concentration of 0.05 to 20 times the reducing agent concentration used, preferably 0.1 to 10 times, particularly 0.2 to 1.0 times, especially 0.3 to 0.6 times. Thus it will generally be added to a concentration of 0.05 to 200 mM, especially 0.2 to 15 mM, particularly 0.2 to 1.0 mM for dithiol binding agents (e.g. maleimides) and 0.2 to 200 mM, especially 1 to 100 mM, particularly 5 to 15 mM for organic disulphides (e.g. cystamine).

The biological fluid sample used in the assay of the invention is conveniently a blood or blood derived sample, e.g. plasma or serum, although other biological fluids may be used if desired. The sample is preferably cell-free, e.g. being prepared by centrifugation, filtration, or by lysis.

The assays of the invention preferably involve the use of a second enzyme for which a product of the enzyme-mediated homocysteine conversion is a substrate. If necessary further enzymes or other systems may be used to generate a directly detectable analyte. Especially preferably the second enzyme is lactate dehydrogenase (LDH), which in the presence of nicotinamide adenine dinucleotide (NADH) converts α-ketobutyrate to α-oxo-butyrate and NAD$^+$. NAD$^+$ can be detected by a colour generating cycling reaction as described in WO 98/07872 (Glasgow) and in the Examples below.

The neutralization or depotentiation of DTT in such HCy assays significantly improves the assay result by reducing background; however there is still room for further improvement.

The homocysteine desulphurase enzyme used in such HCy assays is generally unstable on storage in aqueous solution and thus are generally provided in lyophilized form, e.g. using albumin, for example bovine serum albumin (BSA) as the cryo/lyoprotectant. We have now surprisingly found that assay background may be reduced by avoiding use of BSA, e.g. by use instead of thiol-free cryo/lyoprotectants, e.g. thiol-free albumin, immunoglobulins, polyalkyleneoxides (e.g. PEG), or sugars such as trehalose and maltose.

Thus viewed from a further aspect the invention provides a homocysteine assay which comprises contacting a biological fluid sample with a liquid reagent containing a homocysteine converting enzyme, especially HDS, wherein said reagent is produced by adding an aqueous liquid to a lyophilisate containing said enzyme and a cryo/lyoprotectant, characterised in that said lyophilisate is substantially free of thiol-containing cryo/lyoprotectants.

In this aspect of the invention, the enzymes used may be enzymes as described in WO 93/15220 (Axis), WO 98/07872 (Glasgow), U.S. Pat. No. 5,985,540 (Anti Cancer), U.S. Pat. No. 5,885,767 (Biocatalytics), U.S. Pat. No. 5,998,191 (Anti Cancer), and the publications referred to therein.

The homocysteine converting enzyme is preferably one which removes or converts the thiol group in HCy. Examples of homocysteine converting enzymes include S-adenosyl homocysteine hydrolase (SAHH), homocysteinase or homocysteine desulphurase (HDS), dimethylthetin-homocysteine methyl transferase (DHMT), methionine synthetase (MS) and cystathionine β-synthetase (CβS). Preferably however the enzyme is homocysteine desulphurase (HDS), which converts homocysteine to α-ketobutyrate.

Examples of suitable cryo/lyoprotectants (otherwise referred to as bulking agents or stabilizers) include thiol-free albumin, immunoglobulins, polyalkyleneoxides (e.g. PEG), trehalose, mannitol, glucose, maltose, raffinose and stachyose. (See for example WO 97/29782). These can be used in conventional amounts in conventional lyophilization techniques.

This second aspect of the invention is especially preferably used in combination with the first aspect of the invention.

Where second or further enzymes are used in lyophilised form, these too are preferably prepared using thiol-free cryo/lyoprotectants.

Alternatively the HDS containing reagent may be provided as a liquid containing a thiol-reducing agent (e.g. DTT, DTE, TCEP, etc.), together with a proteinaceous or non-proteinaceous stabilizer, e.g. thiol-free albumin (e.g. DTT or TCEP treated albumin) or immunoglobulin (e.g. IgG, for example bovine gamma globulin), peptones or a polyalkylene oxide (such as a PEG) or a polyol such as a fatty acid ester (e.g. $C_{16-22}$, especially $C_{18}$ fatty acid) of a polyol (especially a $C_6$ polyol) or a polyoxyethylated derivative thereof (e.g. a Span or Tween nonionic surfactant such as Tween 20), a carbohydrate or polysaccharide. In general, proteinaceous stabilizers should be used at concentrations of up to 10% wt, e.g. 0.01 to 10%, preferably 0.01 to 1%, more preferably 0.02 to 0.5%, e.g. 0.05 to 2 mg/mL.

Thus viewed from a further aspect the invention provides a homocysteine assay which comprises contacting a biological fluid sample with a liquid reagent containing homocysteine desulphurase, wherein said liquid reagent is an aqueous liquid containing homocysteine desulphurase, a thiol-reducing reagent (e.g. at 0.05 to 20 mM, especially 0.05 to 15 mM, preferably 1 to 10 mM), and a proteinaceous or non-proteinaceous stabilizer (e.g. at 0.01 to 10% wt, preferably 0.01 to 1%, more preferably 0.02 to 0.5%).

The three aspects of the invention described above serve to reduce the background signal level, i.e. the signal generated by performance of the assay in the absence of the homocysteine conversion enzyme. However again there is still room for further improvement.

It has surprisingly been found that background levels may be reduced still further by treatment of the biological fluid sample to remove pyruvates and other keto acids.

Thus viewed from a further aspect the invention provides a homocysteine assay which comprises contacting a biological fluid sample with a homocysteine converting enzyme, characterised in that before contact with said enzyme said sample is treated with an agent which serves to deactivate pyruvates, e.g. by immobilizing, binding or converting pyruvates.

Examples of agents which deactivate pyruvates include non-enzymatic agents such as thiamine, alkaline hydrogen peroxide, dichloromethyl ether, air or oxygen, or nucleophiles such as hydrazine, semicarbazide and hydroxylamines and enzymes such as pyruvate carboxylase, pyruvate oxidase, malate dehydrogenase, transaminases, acetoacetate decarboxylase, lactate dehydrogenase, pyruvate decarboxylase, 2-ketobutyrate dehydrogenase, alanine transaminase, acetolactate synthase, 2-ethylmalate synthase, urocanate hydralase, cystathione lyase, methylalanine dehydrogenase, N5-(carboxyethyl)-ornithine synthase, methylmalonyl Co-A carboxy transferase, glutamine-pyruvate transaminase, pyridoxamine-pyruvate transaminase, serine-pyruvate transaminase, lysine-pyruvate transaminase, ATP: pyruvate 2-O-phosphotransferase, and especially alanine amino transferase and pyruvate dehydrogenase. Thiamine promotes non-enzymatic decarboxylation of pyruvates. Hydrazines serve to trap pyruvates. Pyruvate decarboxylase and the coenzyme thiamine pyrophosphate convert pyruvate to acetaldehyde and $CO_2$. Alanine amino transferase, together with glutamate and pyridoxyl-5-phosphate, converts pyruvates to 2-oxo-glutarate and L-alanine, and pyruvate dehydrogenase converts pyruvates to acetyl Co-A.

If the agent used to deactivate pyruvate is hydrogen peroxide, it will be understood that the hydrogen peroxide will need to be neutralised prior to contacting the sample with said enzyme. Any suitable reagent i.e. antioxidant or enzyme may be used, but preferably the hydrogen peroxide is neutralised using catalase, which catalyzes the following reaction: $2H_2O_2 \rightarrow 2H_2O+O_2$.

Preferably, hydrogen peroxide is added to the sample at 0.01% to 1% final concentration, preferably 0.05% to 0.5% and most preferably 0.1 to 0.3%. Catalase is added after the removal of pyruvate at 10 to 500 U/ml, preferably 50 to 400 U/ml, most preferably 80 to 300 U/ml.

Some pyruvate-converting enzymes such as malate dehydrogenase and pyruvate dehydrogenase are NAD dependent for their action and thus may be less preferred where the homocysteine assay involves a NAD dependant signal generation step.

Enzymatic pyruvate-converting agents will generally be preferred over non-enzymatic agents due to their relative specificity as a result of which any excess agent will not give rise to undesired effects later in the assay procedure. Thus for example where hydrazine is used and the homocysteine assay involves use of HDS to generate a-ketobutyrate, the a-ketobutyrate must be protected by removal of any remaining hydrazines or other nucleophiles, e.g. by addition of ketones or more preferably aldehydes (e.g. acetone or formaldehyde) in stoichiometric amounts after the pyruvate-conversion step.

Typically, the biological fluid sample will be contacted with: 0.1 to 20 mM hydrazine (especially 0.1 to 15 mM, particularly 0.5 to 10 mM); 20 to 150 µM glutamate (especially 25 to 100 µM, particularly 30 to 80 µM), 1 to 100 µM pyridoxyl-5-phosphate (especially 5 to 80 µM, particularly 10 to 50 µM) and 5 to 50 IU alanine amino transferase; 1 to 100 mM pyruvate dehydrogenase (especially 1 to 60 mM, particularly 5 to 50 mM) and 1 to 100 µM Co Enzyme A (especially 5 to 80 µM, particularly 10 to 50 µM); or 1 to 100 mM pyruvate decarboxylase (especially 1 to 60 mM, particularly 5 to 50 mM) and 1 to 100 µM thiamine pyrophosphate (especially 5 to 80 µM, particularly 10 to 50 µM). Appropriate concentrations for such pyruvate-deactivating agents can be determined by routine experimentation on pyruvate-containing biological fluid samples.

Pyruvate removal may be effected using several reagents and several treatment steps if desired. Thus such treatment may for example involve:

i) pre-treatment of patient samples with acid (e.g. 1M HCl) followed by centrifugation and subsequent use in the assay of the supernatant. The acid will typically be added to achieve a concentration in the supernatant of 0.1 to 1M, preferably 0.2 to 0.5M, especially 0.2 to 0.3M;

ii) heat-treatment, e.g. to 37 to 100° C., preferably 37 to 80° C., more preferably 40 to 60° C., of the plasma or serum;

iii) esterification of pyruvic acid, e.g. by addition of ethanol and HCl;

iv) removal of carboxylic acid groups, e.g by addition of 0.1 to 3 mg/mL EDAC, preferably 0.1 to 2 mg/mL, especially 0.5 to 1.5 mg/mL, and Tris buffer, e.g. 0.1 mM Tris, pH 7;

v) addition of semicarbazide, e.g. to a concentration of 0.01 to 10 mM, preferably 0.1 to 5 mM, especially 0.2 to 2 mM;

vi) addition of hydroxylamine, e.g. to a concentration of 0.01 to 10 mM, preferably 0.1 to 5 mM, especially 0.2 to 2 mM.

vii) pretreatment with LDH (generally to a concentration of 10 to 40 µg/mL, preferably 12 to 30 µg/mL, especially 15 to 25 µg/mL) and NADH (generally 20 to 80 µM, preferably 45 to 55 µM) to convert pyruvate to lactate, and heat treatment (e.g. as above preferably in the presence of nitrous acid) to remove NAD+;

viii) pre-treatment with β-naphthylamine (generally to a concentration of 0.1 to 10 mg/mL, preferably 0.1 to 5 mg/mL, especially 0.2 to 1 mg/mL);

ix) if required treatment to remove NAD, e.g. by heating as described above, heating in an acid environment, or exposure to ultraviolet light; and x) pre-treatment of patient samples via exclusion filtration followed by centrifugation in order to remove pyruvate and other keto acids. Any suitable filter may be used.

Pyruvate removal may be effected using size exclusion filters, together with centrifugation. Any suitable exclusion filter may be used, e.g. 10 kD to 60 kD exclusion filter, preferably 20 to 50 kD, most preferably 30 kD. Use of exclusion filtration followed by centrifugation prior to the addition of the homocysteine converting enzyme forms a preferred aspect of the invention.

Filtering the biological fluid sample through a molecular sieve in order to remove or reduce background signals in the enzymatic homocysteine assay forms a preferred aspect of the invention.

Following the deactivation of pyruvate, it forms a preferred aspect of the invention to heat the sample, e.g. to 37 to 100° C., preferably 37 to 80° C., more preferably 40 to 60° C., for 5 to 100 minutes, preferably 10 to 80 minutes, more preferably 15 to 60 minutes. It forms a further preferred aspect if the pyruvate deactivating agent used prior to heat treatment is hydrogen peroxide.

This aspect of the assay of the invention may be performed using any of the homocysteine converting enzymes mentioned in the publications referred to above, especially HDS. This aspect of the invention is preferably used together with the first, second or third aspects, especially with both the first and second or first and third aspects.

Preferably, a microtitre plate is used in any of the aspects of the invention.

Further, the use of immobilized homocysteine converting enzymes may allow the removal of pyruvate from the serum.

Thus, viewed from a further aspect the invention provides a homocysteine assay which comprises contacting a biological fluid sample with an immobilized homocysteine converting enzyme, especially HDS, wherein said biological fluid sample contacts the immobilized enzyme under such time and conditions to allow the homocysteine in the sample to bind to said enzyme, characterised in that the biological fluid sample is then removed from the assay.

In this aspect of the invention, the enzymes used may be as described previously. Preferably however the enzyme is HDS.

The homocysteine-converting enzyme may be immobilized by any suitable technique well known in the art. Preferably said homocysteine converting enzyme is attached to a solid support, via any suitable linkage. As used herein "linkage" refers to any interaction between the homocysteine converting enzyme and the solid support, enabling them to be associated. Such interaction may involve physical association such as covalent binding and may also involve so-called "weak" interactions such as hydrogen bonds, Van der Waals forces and ionic interactions. Alternatively, the homocysteine converting enzymes may be provided with means for attachment to a solid support. Such means may constitute or comprise, for example, one partner of an affinity binding pair, e.g. biotin, binding to the corresponding binding partner of the affinity binding pair, i.e. streptavidin, provided on the solid support. DNA:DNA binding proteins and antibodies:antigens may also be used as alternative binding pairs.

Alternatively, the solid support may be provided with means for attachment to a homocysteine converting enzyme. Suitable means include immobilized antibodies or fragments thereof, amine binding ligands or protein binding ligands e.g. plates coated with chelating nickel which are commercially available e.g. plates coated with chelating nickel which are commercially available (Qiagen Ltd, UK). In order to create an amine binding surface the solid support may be succinimide activated microtitre plates can either be coated with succinimide, or are commercially available (Pierce Chemical Company, US).

The solid support may be any of the well known supports or matrices which are currently widely used or proposed for immobilisation, separation, etc. These may take the form of particles, sheets, dipsticks, gels, filters, membranes, fibres, capillaries or microtitre strips, tubes, plates or wells etc.

Conveniently, the support may comprise glass, silica, latex or a polymeric material as for example nitrocellulose, teflon, alginate, agarose, polystyrene, latex or nylon. Preferred are materials presenting a high surface area for binding.

Preferably, a microtitre plate may be used in the method of the invention.

The attachment of the homocysteine converting enzyme to a solid support allows easy manipulation of the enzyme. Thus, the attachment to some kind of solid support can enable the separation of the homocysteine from the rest of the components in the sample, including pyruvate. This can be achieved for example by carrying out washing steps.

The attachment of the homocysteine converting enzyme to a solid support avoids the need to use the lyophilised form of the enzyme.

Preferably, the biological fluid sample is treated with a reducing agent such as DTT, DTE or TCEP prior to contact with the immobilized homocysteine converting enzyme, in order to release covalently bound homocysteine. The sample is then contacted with the immobilized enzyme under such conditions to allow homocysteine to binding to said enzyme, i.e. for 0.5 to 10 minutes, preferably 1 to 8 minutes, more preferably 1 to 5 minutes. Once the homocysteine has bound to the homocysteine converting enzyme, the solid support may be washed in order to remove the biological fluid sample. The solid support is washed using any suitable fluid, preferably a buffer solution, most preferably phosphate buffer.

After the biological fluid sample has been removed from the immobilized enzyme, the assay may be as described previously.

Preferably, the immobilized enzyme is HDS. In order to facilitate the method of this aspect of the invention, the active site or substrate binding site of the enzyme have been engineered by any suitable means, for example via genetic engineering of recombinant enzyme DNA, or by chemical treatment of the homocysteine converting enzyme, in order to chemically alter the active or binding site. With regard to HDS, treatment of the immobilized enzyme with hydrazine prior to contacting the enzyme with the biological fluid sample, removes pyridoxal 5 phosphate from the active site of the enzyme. Once the biological fluid sample has been removed from the immobilized homocysteine sample, the pyridoxal 5 phosphate moiety can be reintroduced. Removal of the pyridoxal 5 phosphate moiety from the active site of the HDS enzyme allows homocysteine to bind to HDS, but no reaction can take place until the pyridoxal-5-phosphate moiety is replaced. Therefore, the engineering of the enzyme to allow binding of homocysteine, but preventing the further enzymatic reaction, is a preferred aspect of the invention. Once the pyruvate has been removed via washing, the enzyme is treated to enable the reaction to proceed.

This aspect of the invention is preferably used together with the first aspect of the invention.

Where the biological fluid on which an enzymatic homocysteine assay is carried out is serum or plasma, we have also found that background, or more precisely patient-to-patient background variation, may be reduced if the cells are removed from the sample rapidly after blood collection, preferably within 60 minutes, more preferably within 30 minutes or less (i.e. 25, 20, 15, 10, 5 minutes or less). Accordingly it is proposed that blood samples for enzymatic assay for homocysteine should be filtered cell free, e.g. through a needle equipped with a filter, within 60 minutes of collection. This forms a further aspect of the present invention.

Viewed from this aspect the invention provides an enzymatic assay for homocysteine in a blood sample, characterised in that said sample is filtered cell-free (i.e. red and white blood cell free) within 60 minutes, preferably within 30 minutes, of being withdrawn from the patient.

Filtering according to this aspect of the invention may be effected by passing the blood sample through a filter, for example a filter in a syringe needle base or in a sample receiving tube, or by absorption in an absorbent web followed by compression of the wetted web to expel a cell-free fluid sample.

The background in a enzymatic homocysteine assay may be determined by performing the assay without use of the homocysteine converting enzyme.

In the assays of the invention, the homocysteine concentration may be determined in a qualitative, semi-quantitative or quantitative manner, e.g. as an absolute concentration or as an indication that concentration is above or below a threshold value or inside or outside a particular range. Total homocysteine concentration will generally be determined; however if desired treatment with a reducing agent such as DTT, DTE or TCEP may be omitted and the free homocysteine concentration may instead be determined. To allow quantitative determination, the assay will preferably be calibrated by being run with standards containing homocysteine at a known concentration or more preferably a series of known concentrations. The background signals for the various samples tested will likewise preferably be determined so that a corrected signal may be generated by subtraction of the background signal from the detected signal. Preferably sample signals, background signals and calibration signals will be detected following performance of the assay for the same period of time, i.e. after allowing signal to build up for the same period of time. For each type of assay, the optimum period of time for signal build up may be determined readily by following the time-dependence of signal and background development. Such an optimum may obviously be a balance between signal value and assay duration, especially where the assay is performed on automated apparatus.

The signal determined in the assay will depend on the nature of the reaction used to generate the signal. Thus the signal will generally be a radiation (e.g. light) absorption, emission or scattering. In the examples below, the signal is the light absorption (generally measured at 550 nm) by the colored formazan compound generated from a colourless tetrazolium salt. In this particularly preferred form of the assay of the invention, the following process steps and reactions occur:

1. A blood sample is collected and separated into plasma or serum.
2. The cells from the sample are removed, preferably within 60 minutes, more preferably within 30 minutes, e.g. by centrifugation or filtration.
3. The resultant plasma or serum sample is preferably treated with a pyruvate removing agent, e.g. hydrogen peroxide.
4. Excess pyruvate removing agent is removed (i.e. excess hydrogen peroxide is removed with catalase).
5. The sample is preferably treated with a reducing agent, especially preferably dithiothreitol (DTT), dithioerythrol (DTE), or triscarboxyethylphosphine (TCEP) to release covalently bound homocysteine.
6. The sample is contacted with HDS to convert HCy to α-ketobutyrate, $H_2S$ and ammonia.

7. The HDS-treated sample is preferably treated with an organic disulphide (especially where a non-sulphide reducing agent is used in step (4)), or an oxidizing agent (e.g. perchloric acid, iodate or periodate), or more preferably a DTT binding agent (e.g. a maleimide), to bind or destroy excess reducing agent.
8. The sample is contacted with NADH and lactate dehydrogenase (LDH) and incubated to convert α-ketobutyrate and NADH to α-hydroxybutyrate and $NAD^+$.
10. The sample is acidified to remove excess NADH and then brought to neutral pH.
11. The sample is contacted with ethanol, a tetrazolium salt, alcohol dehydrogenase (ADH) and an oxidizing agent causing an $NAD^+$/NADH cycling reaction where $NAD^+$ and ethanol are converted to NADH and acetaldehyde and NADH and the tetrazolum salt are converted to $NAD^+$ and formazan. The mixture is incubated and the formazan concentration is measured by light absorption at 550 nm, generally after addition of acid to destroy NADH and stop the cycling reaction.

In the scheme set out above, the sample is referred to as being contacted with the various reagents at the relevant stages of the reaction scheme. However in order to reduce the total number of reagent solutions required, certain reagents may and generally will be added at earlier stages.

Viewed from a further aspect, the invention also provides a kit for a homocysteine assay, said kit comprising:

homocysteine desulphurase, preferably (i) in lyophilized form, the lyophilisate being substantially free of thiol-containing cryo/lyoprotectants or (ii) in aqueous liquid form further containing a dithiol reducing agent (e.g. DTT, DTE or TCEP) and a proteinaceous or non-proteinaceous stabilizer;

a L-homocyst(e)ine (or L homocysteine precursor) standard, preferably a plurality of standards containing L-HCy or L-homocystine (or a precursor) at a plurality of known concentrations;

a reducing agent, e.g. dithiothreitol, dithioerythiol, TCEP or methyl iodide;

an agent which binds, oxidizes or depotentiates the reducing agent, e.g. an organic disulphide or a dithiol binding agent, preferably a maleimide;

optionally one or more further reagents capable of converting the homocysteine conversion product of HDS into a detectable analyte (e.g. LDH, NADH, ADH, a tetrazolum salt, an oxidizing agent, and an acid);

preferably a pyruvate deactivating agent, e.g. hydrazine, acetoacetate decarboxylase, pyruvate carboxylase, hydrogen peroxide or pyruvate dehydrogenase;

optionally one or more additional reagents capable of removing/inactivating the pyruvate deactivating agent, i.e. catalase; and optionally a filter capable of removing red blood cells from blood.

The publications mentioned herein are hereby incorporated by reference.

Figure 1:
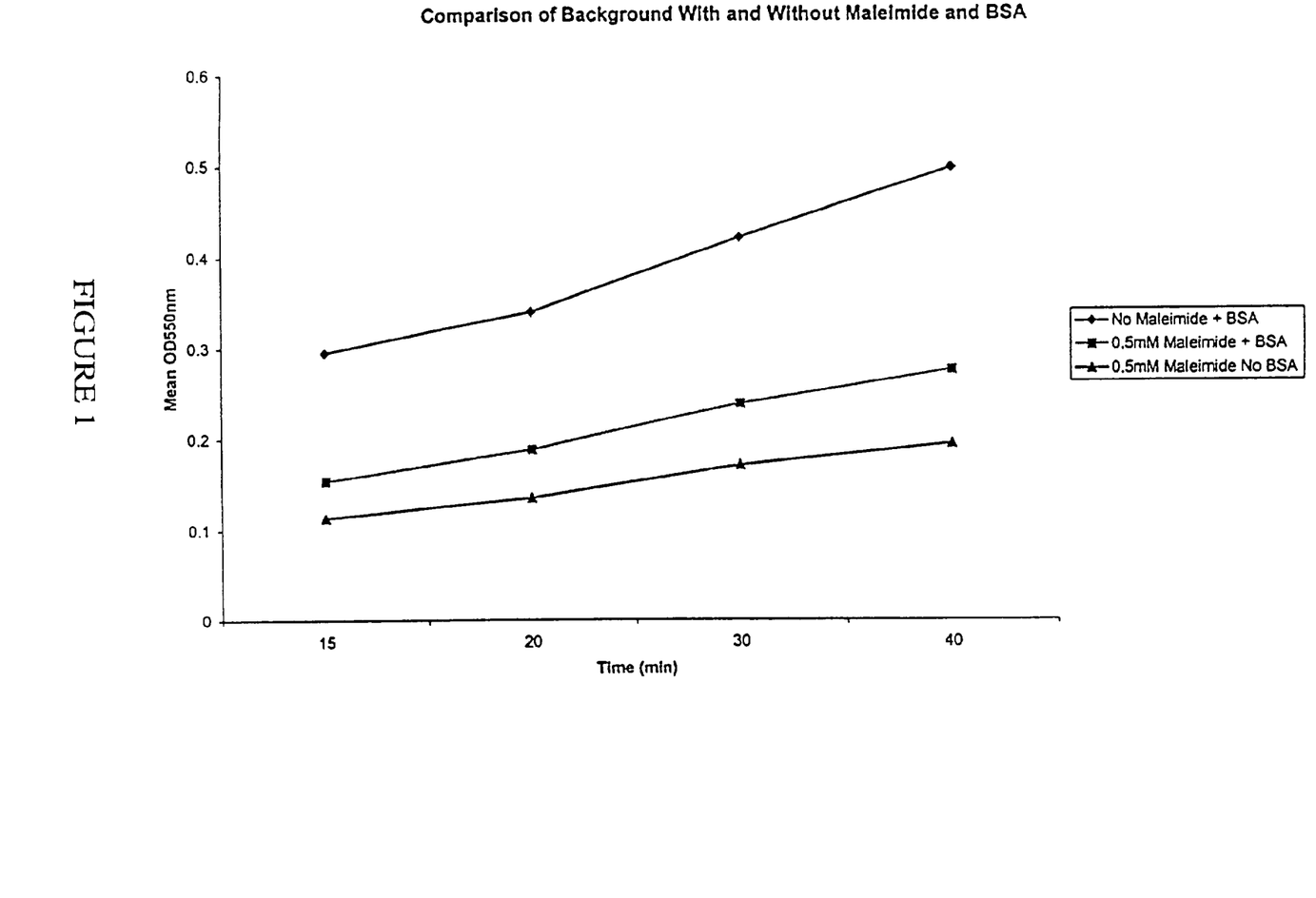
FIG. 1 shows the effect of reducing agent removal on the background signal in a Hcy assay.
Figure 2:
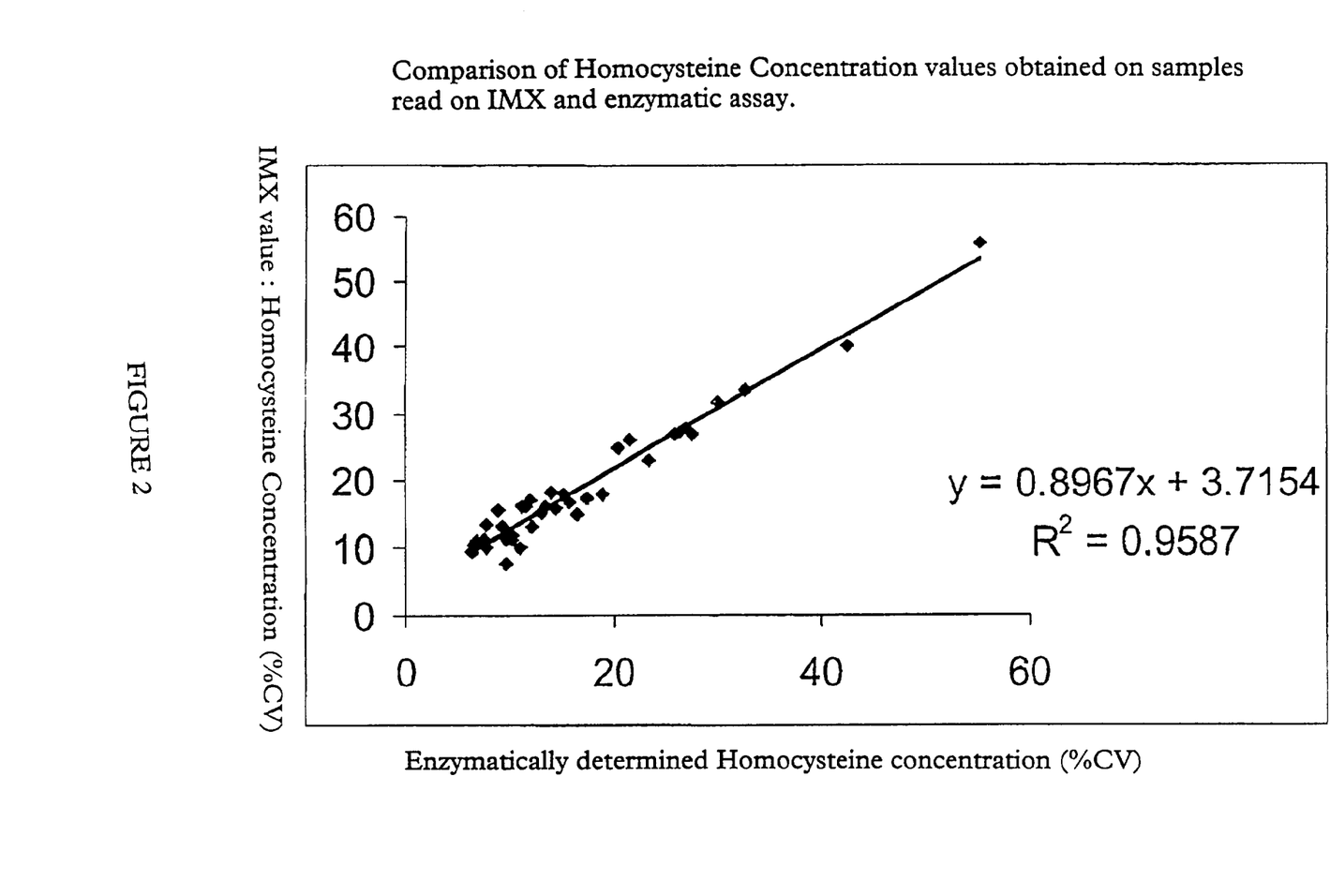
FIG. 2 shows the correlation of the assay of the invention with a commercial Hcy essay.

The invention will now be illustrated further by the following non-limiting Examples, with reference to the drawings in which:

FIG. 1 shows the comparison of background signal with and without maleimide and BSA, as a plot of mean OD 550 nm versus time in minutes. Three plots are shown, demonstrating the data obtained from Example 5, (A) ♦ no maleimide plus BSA, (B) ■ maleimide plus BSA and (C) ▲ maleimide without BSA. The experimental conditions are defined in Example 5;

FIG. 2 shows the correlation of results from homocysteine-containing samples from Example 6 read on IMX and by the enzymatic method, as a plot of IMX value versus estimated concentration via enzymatic assay in μM. The experimental conditions are defined in Examples 6, 7 and 8.

Figure 3:
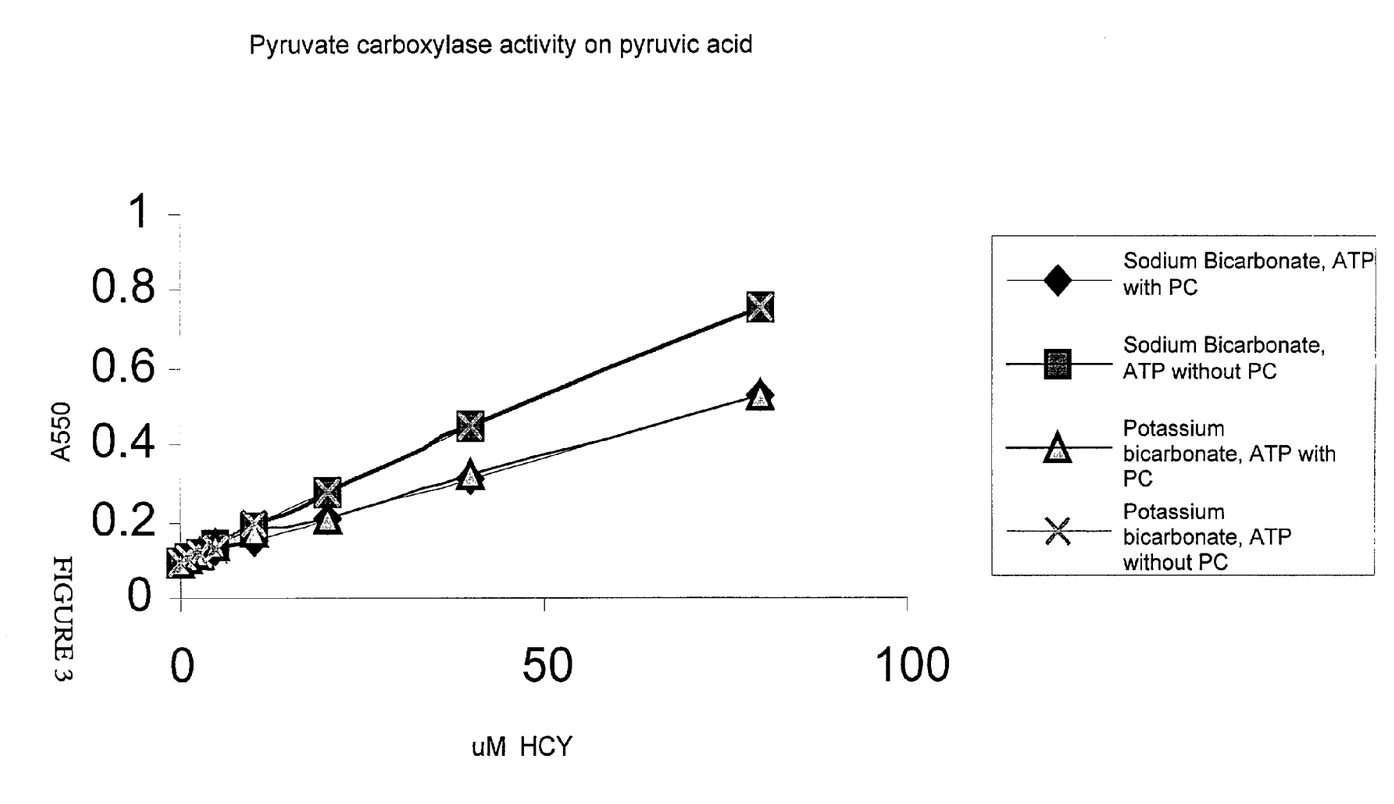
FIG. 3 shows the effect of pyruvate carboxylase in a Hcy assay.
Figure 4:
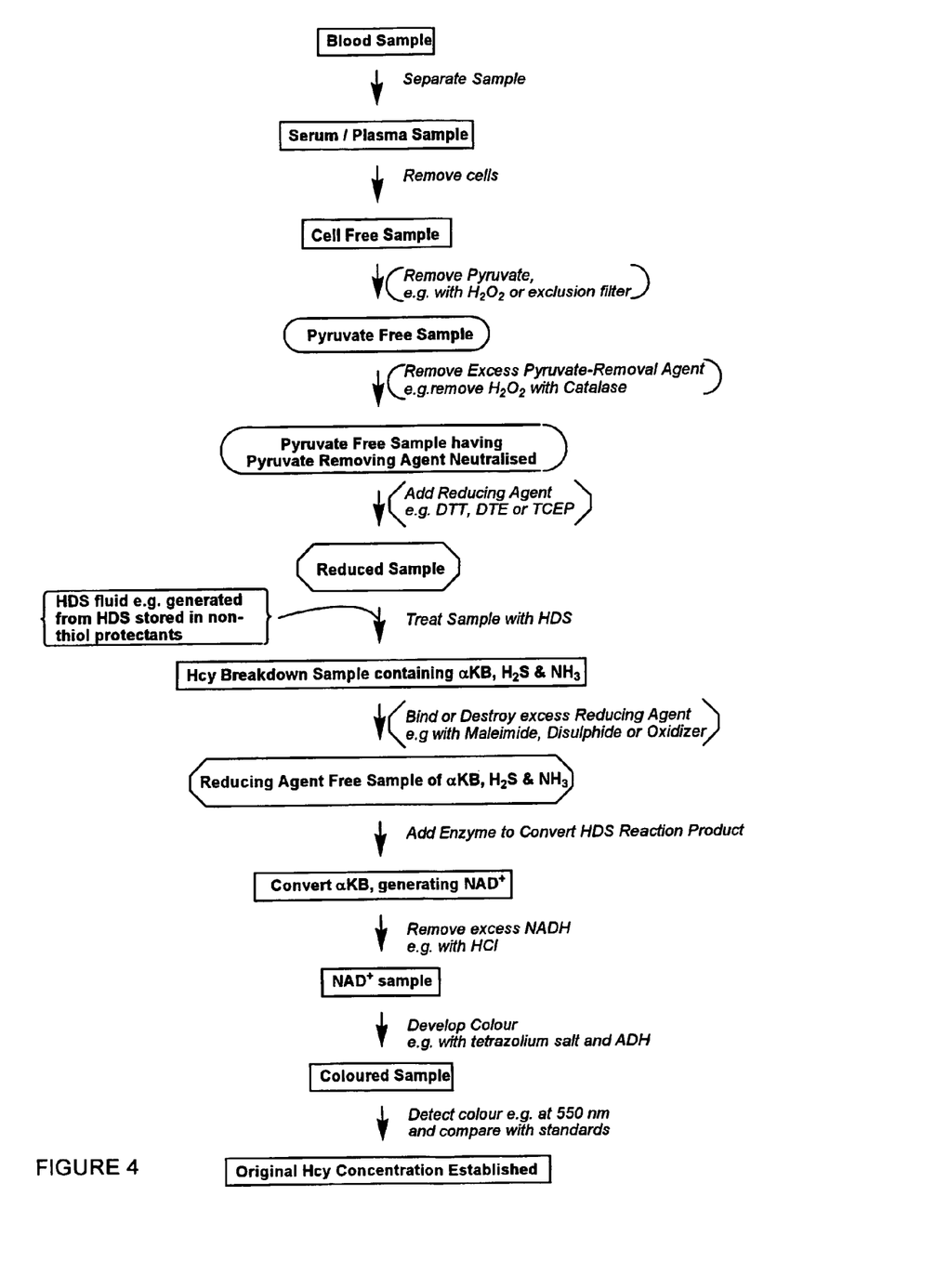
FIG. 4 shows a flow diagram of various steps involved in embodiments of the invention.

FIG. 3 shows the results from Example 6, the effect of removal of pyruvate with pyruvate carboxylase, as a plot of OD 550 nm versus concentration of homocysteine in μm. Four plots are shown, ♦ sodium bicarbonate, ATP and pyruvate carboxylase, ■ sodium bicarbonate, ATP without pyruvate carboxylase, ▲ potassium bicarbonate, ATP and pyruvate carboxylase, and X potassium bicarbonate, ATP without pyruvate carboxylase.

EXAMPLE 1

Assay Reagents
A) Pyruvate and keto acid remover 0.47% Hydrogen peroxide (Can use 0.47% to 10%)

| B) Enzyme Reagent 1 | |
| --- | --- |
| Homocysteine desulphurase | 0.02 U/mL |
| Lactate dehydrogenase | 20.8 μg/mL |
| NADH | 50 μM |
| Cryo/lyoprotectant* | 0.8 wt % |
| Phosphate buffer (pH 8.0) | 0.1 M |
| catalase | 300 U/ml |
| Total volume | 1.5 mL |

*trehalose, gelatin, maltose, dextran, mannitol, Tween 20 or casein

The reagent is in lyophilized form and may be reconstituted with 1.5 mL Ro grade water. It is then stable for 8 hours.

C) Blank Reagent 1
As enzyme reagent 1 but without the homocysteine desulphurase.

D) Reducing reagent
Dithiothreitol 20 mM in aqueous 2.5 mM citric acid, pH 3.0.

E) Reagent 2
190 mM HCl containing 0.55% wt Nonidet P40, 1.5 mM maleimide, and 5.5% ethanol F) Reagent 3
16 μM MPMS (1-methoxy-5-methyl-phenazinium methyl sulfate); 144 μM NBT, 26 U/ml ADH, in 963 mM Tris buffer pH 7.6.

3.25 mL of 0.1 M phosphate buffer, pH 7.0 (0.026 g disodium hydrogen orthophosphate and 0.016 g sodium dihydrogen orthophosphate 1-hydrate, in Ro grade water), containing 1% sucrose (maltose or trehalose) (32 mg), 23.7 U/ml ADH (alcohol dehydrogenase) and 23.9 U/ml MPMS (1-methoxy-5-methyl-phenazinium methyl sulfate). This is freeze-dried and reconstituted in 13 ml of 144 μm NBT (nitroblue tetrazolium) in 1.15M Trizma, pH 7.6

| G) Calibrator | |
| --- | --- |
| To make 1 ml of calibrator | |
| L-Homocysteine | 0.86 mg |
| 6M HCl | 0.50 μl |
| Milli-Ro water | 9.50 μl |

This is added to 990 µl of phosphate buffered saline (0.01 m phosphate buffer containing 0.0027M KCL, 0.137M NaCl, pH 7.4). This is diluted further with phosphate buffered saline to give stable liquid calibrations of 2.5 µM, 5 µM, 10 µM and 20 µM, L-homocysteine which corresponds to 5, 10, 20 and 40 µM L-homocysteine.

H) Stop Solution 6M HCl.

EXAMPLE 2

Assay Protocol

Human blood was collected into vacutainer tubes containing citrate. Plasma was separated from cells upon centrifugation at 1000×g for 10 minutes at 2–8° C.

10 µl of sample is mixed with 10 µl of 0.47% Hydrogen peroxide on a microtitre plate and incubated at room temperature for 3 minutes. 25 µl of Enzyme Reagent 1 is added and incubated for 30 minutes at 37° C. 10 µl of the same sample is mixed with 10 µl of 0.47% Hydrogen peroxide and incubated at room temperature for 3 minutes. 25 µl of Blank Reagent 1 is added and incubated for 30 minutes at 37° C. Following this incubation 85 µl of Reagent 2 is added to each and after mixing they are incubated a further 3 minutes at room temperature.

Reagent 2 contains the DTT binding agent and the acid destroys the excess NADH. 125 µl of reagent 3 is added and incubated at 37° C. for 15 minutes. Reagent 3 brings the pH of the reaction to pH 7.0 and allows ADH to convert ethanol to acetaldehyde thus generating NADH. The NADH is then converted to NAD+ as the colourless tetrazolium salt is converted into the coloured product, aided by the oxidising agent, MPMS. The reaction is stopped by the addition of 15 µl of 6M HCL and the sample is read at 550 nm. The reading obtained for the sample treated with Blank Reagent 1 is subtracted from the reading for the sample treated with Enzyme Reagent 1.

Calibrators are assayed by the same method and a calibration curve is constructed using the delta reading (the reading obtained for the calibrator assayed in the presence of Blank Reagent 1 is subtracted that obtained for the same calibrator assayed in the presence of Enzyme Reagent 1) plotted against the known concentration of the calibrators. The Delta reading obtained for the sample is read from the standard line and a concentration of homocysteine assigned.

EXAMPLE 3

Background Removal

The assay is performed as in Example 2, with the exception of the pre-treatment of samples with Hydrogen peroxide and the absence of Catalase in Reagent 1 for one set of samples. Table 1 represents samples assayed in the presence and absence of $H_2O_2$/Catalase. Each sample was assayed four times with Enzyme reagent 1 and four times with Blank Reagent 1. The concentration of homocysteine in each sample was obtained by subtracting the mean reading obtained for each sample assayed with Blank Regent 1 from the individual readings obtained for each sample assayed in the presence of Enzyme Reagent 1. The results presented in table 1 demonstrate that the background is reduced when samples were assayed in the presence of hydrogen peroxide and Catalase. The reduction in background has improved the precision of the assay by decreasing the percentage CV (coefficient of variance).

TABLE 1

Sample Background and Precision Obtained in the Absence of Hydrogen Peroxide/Catalase

| Samples | Absence of $H_2O_2$/Catalyse | | | Presence of $H_2O_2$/Catalyse | | |
|---|---|---|---|---|---|---|
| | Background reading | [HCY] µM | % CV | Background reading | [HCY] µM | % CV |
| 1 | 1.30 | 3.6 | 57.5 | 0.27 | 8.2 | 8.9 |
| 2 | 1.24 | 2.5 | 63.0 | 0.24 | 17.9 | 5.9 |
| 3 | 1.20 | 5.1 | 40.8 | 0.16 | 13.5 | 3.3 |
| 4 | 1.00 | 7.4 | 19.7 | 0.15 | 12.6 | 9.4 |
| 5 | 0.82 | 22.5 | 11.4 | 0.22 | 38.1 | 1.4 |
| 6 | 1.15 | 3.9 | 64.6 | 0.17 | 10.8 | 4.3 |

[HYC] refers to L-Homocysteine concentration

The results presented in Table 1 were also assayed by the Abbott Imx® Homocysteine assay. The Homocysteine concentrations obtained for these samples are represented in Table 2 when $H_2O_2$/Catalase was not present the correlation was found to be $R^2=0.89$ and in the presence of $H_2O_2$/Catalase the correlation was $R^2=0.99$.

TABLE 2

Homocysteine concentration of samples as determines by Abbot Imx Assay.

| Sample | Homocysteine Concentration (µM) |
|---|---|
| 1 | 8.3 |
| 2 | 15.3 |
| 3 | 13.8 |
| 4 | 11.4 |
| 5 | 39.1 |
| 6 | 11.2 |

EXAMPLE 4

Assay Performance in Comparison to Current Techniques

The assay was performed as in Example 2. A selection of plasma samples including samples from patients with renal failure, samples from healthy volunteers from two sites collected in either citrated or EDTA vacutainers were assayed in the presence of $H_2O_2$/Catalase. Each sample was assayed four times in the presence of Enzyme Reagent 1 and four times in the presence of Blank Reagent 1. The concentration of homocysteine in each sample was obtained by subtracting the mean reading obtained for each sample assayed with Blank Reagent 1 from the individual readings obtained for each sample assayed in the presence of Enzyme Reagent 1. The concentrations obtained were correlated with those obtained in the Abbot Homocysteine IMX assay. The correlation was found to be $R^2=0.96$ and the results are represented in table 3.

TABLE 3

Homocysteine Concentrations. % CV of samples treated with $H_2O_2$ and Catalase

| Sample No. | Specific values (obtained in the presence of enzyme reagent 1) + | + | + | + | Mean blank (in the presence of blank reagent 1) | Estimated conc. (μM) | % CV | Imx value |
|---|---|---|---|---|---|---|---|---|
| A22 | 0.291 | 0.29 | 0.293 | 0.284 | 0.21 | 10.8 | 4.7 | 7.63 |
| A26 | 0.216 | 0.214 | 0.214 | 0.218 | 0.138 | 11 | 2.5 | 6.65 |
| A29 | 0.231 | 0.217 | 0.235 | 0.23 | 0.137 | 13.07 | 8.7 | 12 |
| A31 | 0.282 | 0.28 | 0.284 | 0.276 | 0.168 | 15.9 | 2.7 | 10.97 |
| A32 | 0.275 | 0.269 | 0.281 | 0.272 | 0.161 | 15.9 | 4.1 | 11.5 |
| A36 | 0.279 | 0.284 | 0.281 | 0.272 | 0.206 | 10 | 6.6 | 7.55 |
| A39 | 0.298 | 0.208 | 0.304 | 0.296 | 0.193 | 15.3 | 4.6 | 8.67 |
| A40 | 0.286 | 0.286 | 0.284 | 0.286 | 0.189 | 12.9 | 1 | 9.18 |
| A41 | 0.255 | 0.263 | 0.244 | 0.265 | 0.154 | 14.67 | 9.4 | |
| A42 | 0.229 | 0.23 | 0.222 | 0.222 | 0.154 | 10.16 | 6.2 | 6.52 |
| A44 | 0.247 | 0.248 | 0.243 | 0.243 | 0.139 | 13.4 | 2.6 | 7.57 |
| A45 | 0.249 | 0.254 | 0.251 | 0.253 | 0.173 | 9.8 | 3.1 | 10.9 |
| B47 | 0.411 | 0.411 | 0.423 | 0.404 | 0.277 | 17.9 | 5.7 | 18.82 |
| B57 | 0.53 | 0.533 | 0.55 | 0.569 | 0.185 | 55.8 | 4.9 | 55.25 |
| B73 | 0.365 | 0.375 | 0.368 | 0.326 | 0.186 | 24.7 | 6.4 | 20.4 |
| C8002762 | 0.516 | 0.527 | 0.521 | 0.527 | 0.264 | 40.1 | 2 | 42.47 |
| C8002524 | 0.396 | 0.413 | 0.375 | 0.396 | 0.221 | 27.1 | 8.8 | 26.48 |
| C8002384 | 0.429 | 0.423 | 0.429 | 0.426 | 0.249 | 27.6 | 1.6 | 27.13 |
| C8002610 | 0.426 | 0.444 | 0.445 | 0.438 | 0.236 | 26.8 | 4.2 | 27.69 |
| C8002923 | 0.408 | 0.391 | 0.401 | 0.39 | 0.193 | 26.9 | 4.1 | 25.83 |
| C8003302 | 0.257 | 0.258 | 0.249 | 0.253 | 0.171 | 11.2 | 4.81 | 10.18 |
| C8003316 | 0.33 | 0.334 | 0.353 | 0.334 | 0.247 | 15.1 | 8.9 | 12.98 |
| C8003200 | 0.358 | 0.356 | 0.355 | 0.36 | 0.174 | 25.8 | 1.3 | 2156 |
| C8002545 | 0.448 | 0.461 | 0.466 | 0.472 | 0.226 | 33.5 | 4.5 | 32.78 |
| C8002369 | 0.499 | 0.49 | 0.498 | 0.475 | 0.268 | 31.6 | 5.2 | 30.1 |
| C375262 | 0.29 | 0.301 | 0.307 | 0.307 | 0.176 | 17.88 | 6.5 | 15 |
| C485969 | 0.219 | 0.229 | 0.216 | 0.228 | 0.145 | 11.13 | 8.4 | 9.48 |
| C357556 | 0.355 | 0.338 | 0.347 | 0.329 | 0.221 | 17.3 | 9.4 | 17.4 |
| C515036 | 0.358 | 0.341 | 0.358 | 0.363 | 0.234 | 16.7 | 7.2 | 15.61 |
| C513311 | 0.303 | 0.303 | 0.288 | 0.285 | 0.164 | 18.2 | 6.7 | 13.81 |
| C483375 | 0.341 | 0.351 | 0.355 | 0.366 | 0.185 | 22.9 | 5.7 | 23.52 |
| C489490 | 0.24 | 0.231 | 0.237 | 0.24 | 0.124 | 15.9 | 3.4 | 13.34 |
| D190599 25 | 0.25 | 0.256 | 0.255 | 0.244 | 0.149 | 13 | 5.8 | |
| D190599 32 | 0.168 | 0.17 | 0.169 | 0.175 | 0.11 | 7.4 | 5.4 | 9.48 |
| D190599 28 | 0.217 | 0.21 | 0.214 | 0.212 | 0.151 | 7.9 | 5.6 | |
| D190599 29 | 0.276 | 0.28 | 0.282 | 0.281 | 0.147 | 18.4 | 1.8 | |
| D190599 30 | 0.202 | 0.2 | 0.2 | 0.195 | 0.134 | 8.2 | 5.3 | |
| D190599 31 | 0.197 | 0.202 | 0.196 | 0.194 | 0.126 | 11.2 | 4.6 | 7.4 |
| E701003 | 0.248 | 0.253 | 0.241 | 0.243 | 0.167 | 9.9 | 7.5 | |
| E701008 | 0.359 | 0.361 | 0.366 | 0.359 | 0.231 | 17 | 2.7 | 11.72 |
| E701005 | 0.254 | 0.242 | 0.254 | 0.255 | 0.178 | 9.4 | 9.7 | 6.25 |
| E701006 | 0.302 | 0.306 | 0.301 | 0.293 | 0.189 | 15 | 5.4 | 13.04 |
| E701004 | 0.225 | 0.231 | 0.23 | 0.228 | 0.146 | 12.9 | 3.1 | 9.06 |

The correlation between obtained values and values obtained via Imx have been plotted on FIG. 2.

EXAMPLE 5

Comparative Assay Performance in the Presence/Absence of BSA and DTT

Background signals for homocysteine assays were determined for a centrifuged but unfiltered plasma sample using the LDH and tetrazolium/formazan system of Examples 1 and 2 under three different assay conditions: (A) the blank enzyme reagent 1 contained BSA as the cryo/lyoprotectant, and glutamate, alanine aminotransferase, pyridoxyl-5-phosphate and maleimide were not used; (B) the blank enzyme reagent 1 contained BSA as the cryo/lyoprotectant, glutamate, alanine aminotransferase and pyridoxyl-5-phosphate were not used; and (C) the blank enzyme reagent 1 was used in non-lyophilized solution form with no BSA present, and reagent glutamate, alanine aminotransferase and pyridoxyl-5-phosphate were not used.

The background signals for incubation times of 15 to 40 minutes for (A) ◆, (B) ■ and (C) ▲ are shown in FIG. 1 of the accompanying drawings.

EXAMPLE 6

Assay Protocol

The assay was performed as in Example 2, however in place of pre-treatment of sample with Hydrogen peroxide and the inclusion of Catalase in Reagent 1, the sample is pre-treated with Pyruvate Carboxylase.

The sample is mixed with the following combination of reagents: 100 mM trizma base, pH 7.5, 1 mM ATP (adenosine tri-phosphate), 5 mM magnesium chloride, 15 mM sodium or potassium bicarbonate, 0.1 mM acetyl coenzyme A, 0.117 U/ml pyruvate carboxylase and incubated for 90 minutes at 37° C.

The results from one such study are depicted graphically on FIG. 3. The signals for varying homocysteine concentration of 0 to 100 μM are shown.

EXAMPLE 7

Assay Protocol

The assay is performed as in Example 2, however in place of pre-treatment of sample with hydrogen peroxide and the inclusion of catalase in Reagent 1, the plasma or serum sample is filtered through a 30 kD exclusion filter and centrifuged at 10,000×g for 10 minutes. The assay then proceeds as before. The results showing the reduction in background signal are represented on table 4.

TABLE 4 background signal levels before and after filtration.

| Sample | Background reading before filtration | Background reading after filtration |
|---|---|---|
| 7 | 0.18 | 0.13 |
| 8 | 0.21 | 0.14 |

EXAMPLE 8

Assay Protocol

The assay is performed as in Example 2, however in place of pre-treatment of sample with hydrogen peroxide and the inclusion of catalase in Reagent 1, the sample is pre-treated with pyruvate oxidase.

The sample is mixed in a 1:1 ratio with pyruvate oxidase at 15 U/ml, 5 mM magnesium chloride, 0.1 mM thiamine pyrophosphate, 0.1 mM flavin adenine dinucleotide and incubated at 37° C. for 30 minutes.

EXAMPLE 9

Removal of Background

The assay is performed as in Example 2, however in addition to pre-treatment of the sample, especially a serum sample, the sample is heat treated at 40–60° C. for 15 to 60 minutes. The assay proceeds as before following this step. This additional step removes some of the background left following the removal of Pyruvate and keto acids. The results are represented on table 5.

TABLE 5 background signal levels before and after heat treatment.

| Sample | Background reading before heat treatment | Background reading after heat treatment |
|---|---|---|
| 9 | 0.51 | 0.26 |
| 10 | 0.34 | 0.23 |
| 11 | 0.35 | 0.26 |

EXAMPLE 10

Passive Coating Method

HDS mixed with 0.1M phosphate buffer containing 0.1M NaCl. 50 μl to 300 μl of this solution is added to a microtitre plate, and is incubated for 2 hours. The microtitre plate is then washed 3 times with the same buffer solution and dried in a tunnel drier. To improve stability, an overcoat is added and consists of phosphate buffer (0.1M to 0.5M) containing sucrose (1–10%).

Assay Using Immobilized HDS 1 mM DTT is added to the sample, calibrator or control in order to cleave homocysteine from binding partners. The treated sample is then added to the plate, and incubated for 3 minutes. The plate is then washed with phosphate buffer.

The assay is performed as in Example 2, however, Reagent 1 does not contain HDS as it is bound to the plate.

EXAMPLE 11

Assay Protocol

The assay is performed as in Example 2, however in place of pre-treatment of sample with hydrogen peroxide and the inclusion of catalase in Reagent 1, the plasma or serum sample is pretreated with 20.8 μg/ml LDH and 1 mM NADH and incubated for 30 minutes at 37° C. The NAD+ generated can be destroyed by treatment with Nitrous acid or converted into NADH using 100 U/ml ADH and 5% ethanol.

The ADH can be immobilised on a Sepharose support before it is mixed with the sample and therefore removed from the plasma or serum by centrifugation (2 min. at 2000×g). (Alternatively if ADH is not attached to a Sepharose support its excess activity can be removed by an inhibitor (e.g. tetramethylthiuram disulfide an inhibitor of yeast ADH.))

Results obtained are represented on table 6, using immobilised ADH. The reduction in background signal is represented kinetically with a reduction in slope.

TABLE 6

The effect of LDH pre-treatment and NAD + removal on background

| Sample | Slope (mAU/min at 550 nm) |
|---|---|
| In the presence of immobilised ADH | 14 |
| In the presence of immobilised ADH | 88 |

The invention claimed is:

1. In a method for assaying homocysteine concentration in a biological fluid sample, said method comprising the steps of;
   i) contacting said biological fluid sample with homocysteine desulphurase (HDS) whereby to generate alpha-ketobutyrate,
   ii) generating a signal corresponding to said alpha-ketobutyrate,
   iii) subsequently assessing the thus-generated signal and
   iv) relating the assessed signal to the homocysteine concentration in said biological fluid sample;
   wherein the improvement comprises enhancing the signal to noise ratio by contacting said biological fluid with a reducing agent, prior to step i), subsequently contacting with HDS, in step i), and contacting with an agent which binds, oxidises or renders inactive said reducing agent after step i) and before step ii).

2. The method as claimed in claim 1, said method further comprising;
- adding an aqueous liquid to a lyophilisate comprising HDS and at least one cryoprotectant or lyoprotectant, whereby to provide a liquid reagent and contacting said biological fluid sample with said liquid reagent, wherein said lyophilisate is formed in the substantial absence of any thiol-containing cryoprotectants or lyoprotectants; or
- treating said biological fluid sample with an agent which serves to deactivate pyruvates before contacting with said HDS; or
- contacting said biological fluid sample with an immobillsed HDS under conditions whereby said homocysteine binds to said HDS but does not react, whereby to form bound homocysteine and separating said bound homocysteine from the remainder of said biological sample; or
- filtering said biological fluid sample through a size exclusion filter and centrifuging, whereby to remove pyruvates, before contacting said biological fluid sample with said HDS.

3. The method as claimed in claim 2 wherein said method comprises;
- contacting said biological fluid with a reducing agent, subsequently with HDS and with an agent which binds, oxidizes or renders inactive said reducing agent after being contacted with said HDS and before generating said signal corresponding to said alpha-ketobutyrate;
- adding an aqueous liquid to a lyophilisate comprising HDS and at least one cryoprotectant or lyoprotectant, whereby to provide a liquid reagent and contacting said biological fluid sample with said liquid reagent, wherein said lyophilisate is formed in the substantial absence of any thiol-containing cryoprotectants or lyoprotectants; and
- treating said biological fluid sample with an agent which serves to deactivate pyruvates before contacting with said HDS.

4. The method as claimed in claim 3 wherein said liquid reagent is an aqueous liquid containing homocysteine desulfurase, a thiol-reducing reagent, and a proteinaceous or non-proteinaceous stabilizer.

* * * * *